(12) United States Patent
Legaspi et al.

(10) Patent No.: US 12,274,486 B2
(45) Date of Patent: Apr. 15, 2025

(54) MEDICAL DEVICE AND CONTROL METHOD

(71) Applicant: OLYMPUS CORPORATION, Hachioji (JP)

(72) Inventors: Danilo Legaspi, Hachioji (JP); Tsuyoshi Hayashida, Hachioji (JP); Satoshi Honda, Hachioji (JP); Norihiko Hareyama, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 707 days.

(21) Appl. No.: 17/535,827

(22) Filed: Nov. 26, 2021

(65) Prior Publication Data

US 2022/0079652 A1    Mar. 17, 2022

Related U.S. Application Data

(63) Continuation of application No. PCT/JP2019/021639, filed on May 30, 2019.

(51) Int. Cl.
*A61B 18/12* (2006.01)
*A61B 17/32* (2006.01)
*A61B 18/00* (2006.01)

(52) U.S. Cl.
CPC .......... *A61B 18/1206* (2013.01); *A61B 17/32* (2013.01); *A61B 2018/00642* (2013.01);
(Continued)

(58) Field of Classification Search
CPC ......... A61B 2017/320094; A61B 2018/00642; A61B 2018/00678; A61B 2018/00702;
(Continued)

(56) References Cited

U.S. PATENT DOCUMENTS 9,186,199 B2    11/2015   Strauss et al.
9,320,563 B2    4/2016    Brustad et al.
(Continued)

FOREIGN PATENT DOCUMENTS

JP    2010-533528 A    10/2010
JP    2013-542765 A    11/2013
(Continued)

OTHER PUBLICATIONS

Jul. 23, 2019 Search Report issued in International Patent Application No. PCT/JP2019/021639.
(Continued)

*Primary Examiner* — Tigist S Demie
(74) *Attorney, Agent, or Firm* — Oliff PLC

(57) ABSTRACT

A medical device includes: an end effector configured to apply treatment energy for treating a living tissue according to supplied power; a drive source configured to supply the power to the end effector; and a processor configured to classify, in a first time period after a supply of the power to the end effector is started, the living tissue into any one of a plurality of tissue types based on a first parameter detected in the first time period, control an operation of the drive source after the first time period based on the classified tissue type, reclassify the classified living tissue into any one of the plurality of tissue types based on a second parameter detected after the first time period, and control an operation of the drive source based on the tissue type into which the classified living tissue is reclassified.

19 Claims, 12 Drawing Sheets

(52) U.S. Cl.
CPC ............... *A61B 2018/00678* (2013.01); *A61B 2018/00702* (2013.01); *A61B 2018/00875* (2013.01); *A61B 2018/00904* (2013.01); *A61B 2018/124* (2013.01)

(58) Field of Classification Search
CPC ........... A61B 2018/00761; A61B 2018/00767; A61B 2018/00875; A61B 2018/00892; A61B 2018/00904; A61B 2018/124
See application file for complete search history.

(56) References Cited

U.S. PATENT DOCUMENTS

| | | | |
|---|---|---|---|
| 2010/0198217 A1 | 8/2010 | Strauss et al. | |
| 2012/0136347 A1 | 5/2012 | Brustad et al. | |
| 2012/0283731 A1* | 11/2012 | Unger | A61B 18/1206 606/49 |
| 2017/0000541 A1 | 1/2017 | Yates et al. | |

FOREIGN PATENT DOCUMENTS

| | | |
|---|---|---|
| JP | 6129459 B1 | 5/2017 |
| JP | 2018-519919 A | 7/2018 |

OTHER PUBLICATIONS

Sep. 18, 2023 Office Action issued in Chinese Patent Application No. 201980096572.5.

\* cited by examiner

MEDICAL DEVICE AND CONTROL METHOD

CROSS-REFERENCE TO RELATED APPLICATION

This application is a continuation of International Application No. PCT/JP2019/021639, filed on May 30, 2019, the entire contents of which are incorporated herein by reference.

BACKGROUND

1. Technical Field

The present disclosure relates to a medical device and a control method.

2. Related Art

In the related art, a medical device that treats a living tissue by applying treatment energy to the living tissue from an end effector is known (see, for example, JP 6129459 B1).

In the medical device described in JP 6129459 B1, the end effector applies treatment energy to a living tissue according to supplied power. Furthermore, the medical device controls the operation of the drive source that supplies power to the end effector in a period after a first time period based on the impedance value (hereinafter, referred to as an initial impedance value) of the living tissue detected in the first time period from the start of the supply of power to the end effector.

SUMMARY

In some embodiments, a medical device includes: an end effector configured to apply treatment energy for treating a living tissue according to supplied power; a drive source configured to supply the power to the end effector; and a processor configured to classify, in a first time period after a supply of the power to the end effector is started, the living tissue into any one of a plurality of tissue types based on a first parameter detected in the first time period, control an operation of the drive source after the first time period based on the classified tissue type, reclassify the classified living tissue into any one of the plurality of tissue types based on a second parameter detected after the first time period, and control an operation of the drive source based on the tissue type into which the classified living tissue is reclassified.

In some embodiments, provided is a control method executed by a processor of a medical device. The control method includes: classifying, in a first time period after a supply of power to an end effector configured to apply treatment energy for treating a living tissue according to the supplied power is started, the living tissue to be treated into any one of a plurality of tissue types based on a first parameter detected in the first time period, controlling an operation of a drive source after the first time period based on the classified tissue type, the drive source being configured to supply the power to the end effector; reclassifying the classified living tissue into any one of the plurality of tissue types based on a second parameter detected after the first time period; and controlling an operation of the drive source based on the tissue type into which the classified living tissue is reclassified.

In some embodiments, provided is a control method executed by a processor configured to control a drive source configured to supply power to an end effector configured to apply treatment energy to a plurality of living tissues. The control method includes: controlling the drive source with first treatment energy in a first time period; acquiring a first parameter from impedance detected from the first treatment energy; updating a setting of second treatment energy according to the plurality of living tissues in a second time period after the first time period based on a first determination value and the first parameter; controlling the drive source with the second treatment energy in the second time period; monitoring impedance detected in the second treatment energy with a second determination value; updating a setting of third treatment energy according to the plurality of living tissues in a third time period after the second time period based on an elapsed time of the second time period and a monitoring result of the second determination value; controlling the drive source with the third treatment energy in the third time period; and controlling an operation of the drive source based on impedance detected in the third treatment energy and an elapsed time of the third time period.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
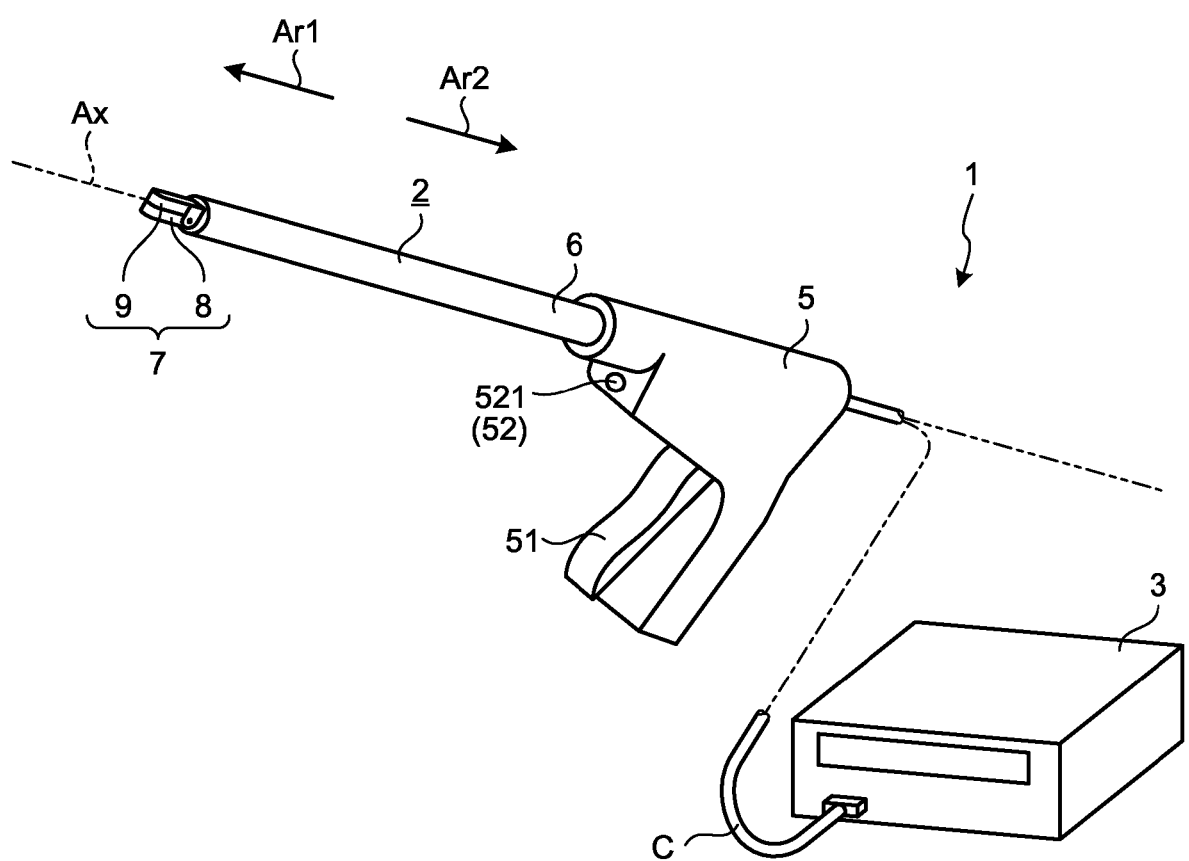
FIG. 1 is a diagram illustrating a treatment system according to an embodiment.

Hereinafter, modes for carrying out the disclosure (embodiments) will be described with reference to the drawings. Note that the disclosure is not limited by the embodiments described below. Further, in the description of the drawings, the same parts will be described with the same reference numerals.

Schematic Configuration of Treatment System

FIG. 1 is a diagram illustrating a treatment system 1 according to the present embodiment.

The treatment system 1 corresponds to a medical device. The treatment system 1 treats a target part (hereinafter, described as a target part) by applying treatment energy to the part to be treated in a living tissue. Here, in the present embodiment, radio frequency energy is employed as the treatment energy. In addition, the treatment that can be performed by the treatment system 1 is sealing of a target part.

As illustrated in FIG. 1, the treatment system 1 includes a treatment instrument 2 and a control device 3.

Configuration of Treatment Instrument

The treatment instrument 2 is, for example, a medical treatment instrument for treating a target part in a state of passing through an abdominal wall. As illustrated in FIG. 1, the treatment instrument 2 includes a handle 5, a shaft 6, and a grip portion 7.

The handle 5 is a portion held by the operator's hand. As illustrated in FIG. 1, the handle 5 includes an operation knob 51 and an interface 52.

The interface 52 is provided in a state of being exposed to the outside from the handle 5, and includes a switch 521 that receives a treatment start operation by the operator. Then, the switch 521 outputs an operation signal according to the treatment start operation to the control device 3 via an electric cable C (FIG. 1).

The shaft 6 has a cylindrical shape, and one end thereof is connected to the handle 5 (FIG. 1). The grip portion 7 is attached to the other end of the shaft 6. An opening and closing mechanism (not illustrated) for opening and closing first and second gripping members 8 and 9 (FIG. 1) constituting the grip portion 7 according to the operation of the operation knob 51 by the operator is provided inside the shaft 6. The electric cable C is disposed inside the shaft 6 from one end to the other end by passing through the handle 5.

Figure 2:
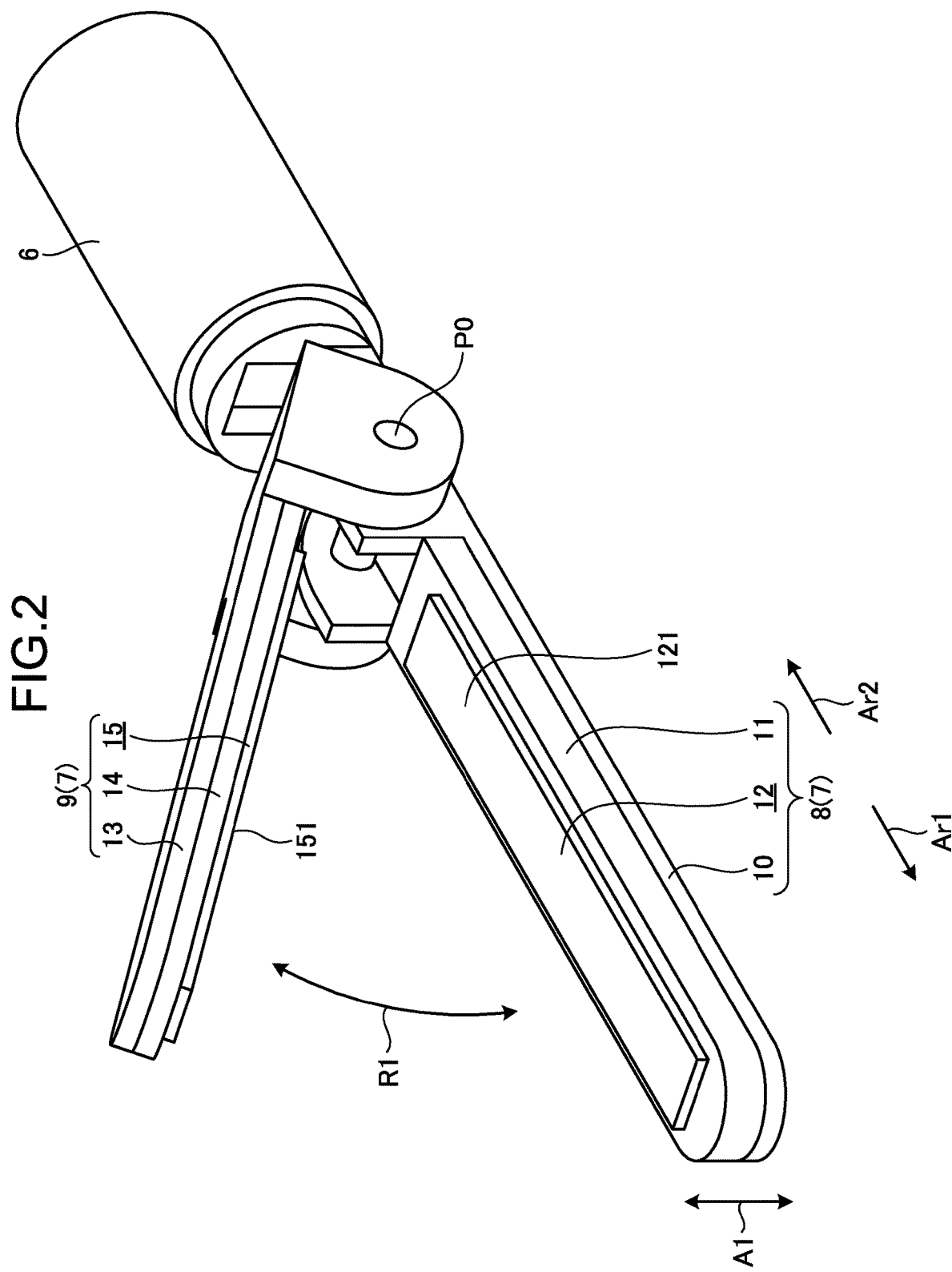
FIG. 2 is a view illustrating a grip portion.

Hereinafter, for convenience of description, one side along the central axis Ax (FIG. 1) of the shaft 6 will be referred to as a distal end side Ar1 (FIG. 1), and the other side will be referred to as a proximal end side Ar2 (FIG. 2).

Configuration of Grip Portion

FIG. 2 is a diagram illustrating the grip portion 7.

The grip portion 7 is a portion that treats a target part while gripping the target part, and corresponds to an end effector. As illustrated in FIG. 1 or 2, the grip portion 7 includes first and second gripping members 8 and 9.

The first and second gripping members 8 and 9 are configured to be openable and closable in a direction of an arrow R1 (FIG. 2) according to an operation of the operation knob 51 by the operator.

Configuration of First Gripping Member

The first gripping member 8 is disposed at a position facing the second gripping member 9. As illustrated in FIG. 2, the first gripping member 8 includes a first jaw 10, a first support member 11, and a first electrode 12.

The first jaw 10 is a portion in which part of the shaft 6 extends toward the distal end, and is formed in an elongated shape extending in a longitudinal direction (a direction along the central axis Ax) from the distal end toward the proximal end of the grip portion 7. The first jaw 10 is made of, for example, a metal material such as stainless steel or titanium. The first jaw 10 supports the first support member 11 and the first electrode 12.

The first support member 11 is an elongated flat plate extending in the longitudinal direction of the grip portion 7, and is made of, for example, a resin material having low thermal conductivity such as polyether ether ketone (PEEK). Then, the first support member 11 is disposed between the first jaw 10 and the first electrode 12.

The first electrode 12 generates radio frequency energy under the control of the control device 3. The first electrode 12 is a flat plate extending in the longitudinal direction of the grip portion 7, and is made of, for example, a conductive material such as copper.

A face of the first electrode 12 on a side of the second gripping member 9 comes into contact with the target part in a state where the target part is gripped by the first and second gripping members 8 and 9. Then, the face of the first electrode 12 functions as a first gripping face 121 (FIG. 2) that applies radio frequency energy to the target part. In the present embodiment, the first gripping face 121 is constituted by a flat face orthogonal to the direction A1 (FIG. 2) in which the first and second gripping members 8 and 9 face each other in a state where the target part is gripped by the first and second gripping members 8 and 9.

One radio frequency lead wire C1 of a pair of radio frequency lead wires C1 and C1' (see FIG. 3) constituting the electric cable C is connected to the first electrode 12.

The first gripping face 121 has a flat face, but is not limited thereto, and may have other shapes such as a convex shape and a concave shape. The same applies to a second gripping face 151 described later.

The first gripping member 8 may be configured by a vibration transmission member (not illustrated) that is connected to an ultrasound transducer (not illustrated) that generates ultrasound vibration, transmits the ultrasound vibration, and applies the ultrasound vibration to the target part. The vibration transmission member together with the second gripping member 9 grips a target part and comes into contact with the target part. In this case, the contact face with the target part is the first gripping face 121 of the vibration transmission member.

In addition, the vibration transmission member may apply ultrasound vibration and apply radio frequency energy to a target part.

Configuration of Second Gripping Member

As illustrated in FIG. 2, the second gripping member 9 includes a second jaw 13, a second support member 14, and a second electrode 15 similar to the first jaw 10, the first support member 11, and the first electrode 12 in the first gripping member 8, respectively.

The proximal end of the second jaw 13 is pivotally supported so as to be rotatable with respect to the shaft 6 about a fulcrum P0 (FIG. 2), and is opened and closed with respect to the first gripping member 8 by being rotated.

In the present embodiment, the first gripping member 8 (first jaw 10) is fixed to the shaft 6, and the second gripping member 9 (second jaw 13) is pivotally supported by the shaft 6, but the disclosure is not limited thereto. For example, both the first and second gripping members 8 and 9 may be pivotally supported by the shaft 6, and the first and second gripping members 8 and 9 may be opened and closed when each is being rotated. Further, for example, a configuration may be employed in which the first gripping member 8 is pivotally supported by the shaft 6, the second gripping member 9 is fixed to the shaft 6, and the first gripping member 8 is rotated to open and close with respect to the second gripping member 9.

A face of the second electrode 15 on a side of the first gripping member 8 functions as the second gripping face 151 that grips the target part with the first gripping face 121. The other radio frequency lead wire C1' is connected to the second electrode 15.

Configuration of Control Device

Figure 3:
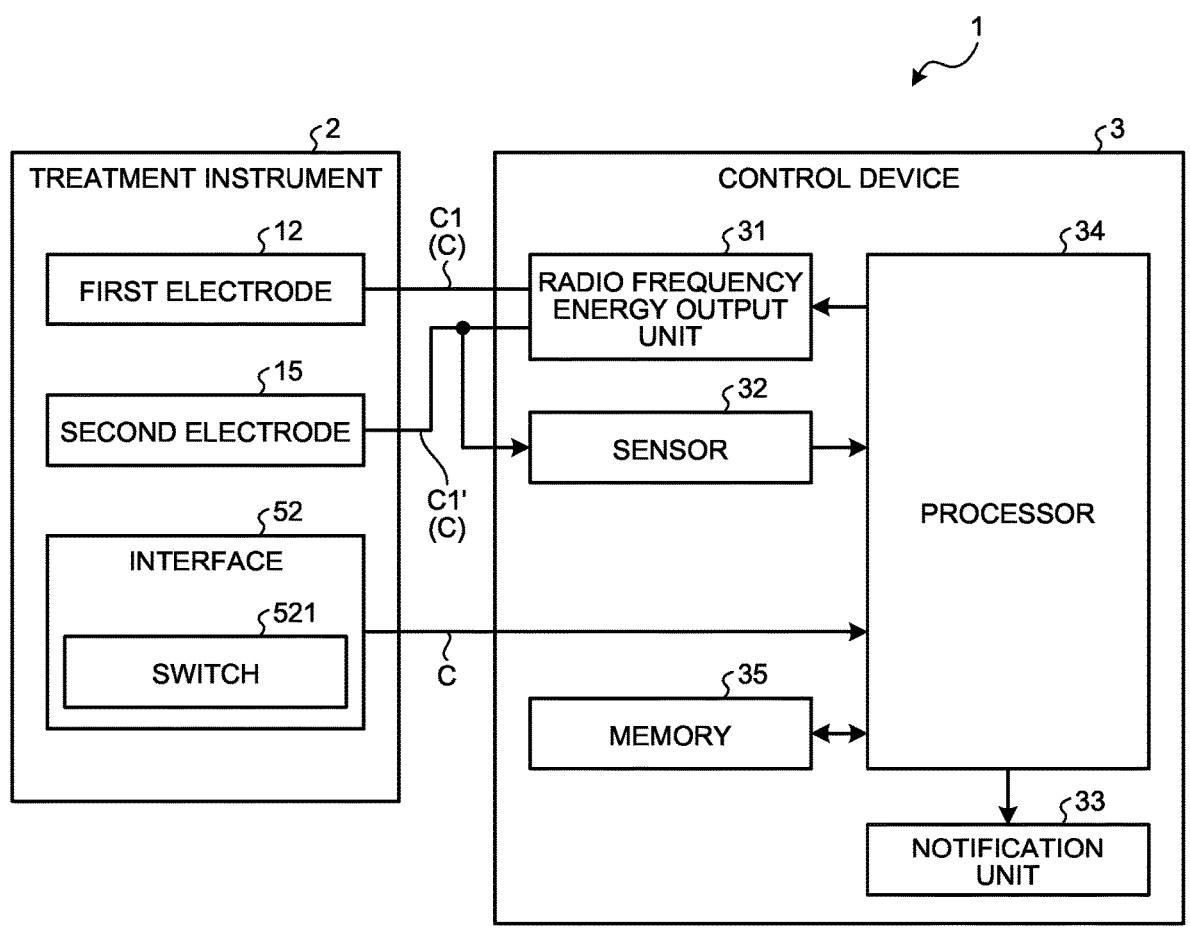
FIG. 3 is a block diagram illustrating a configuration of a control device.
Figure 4:
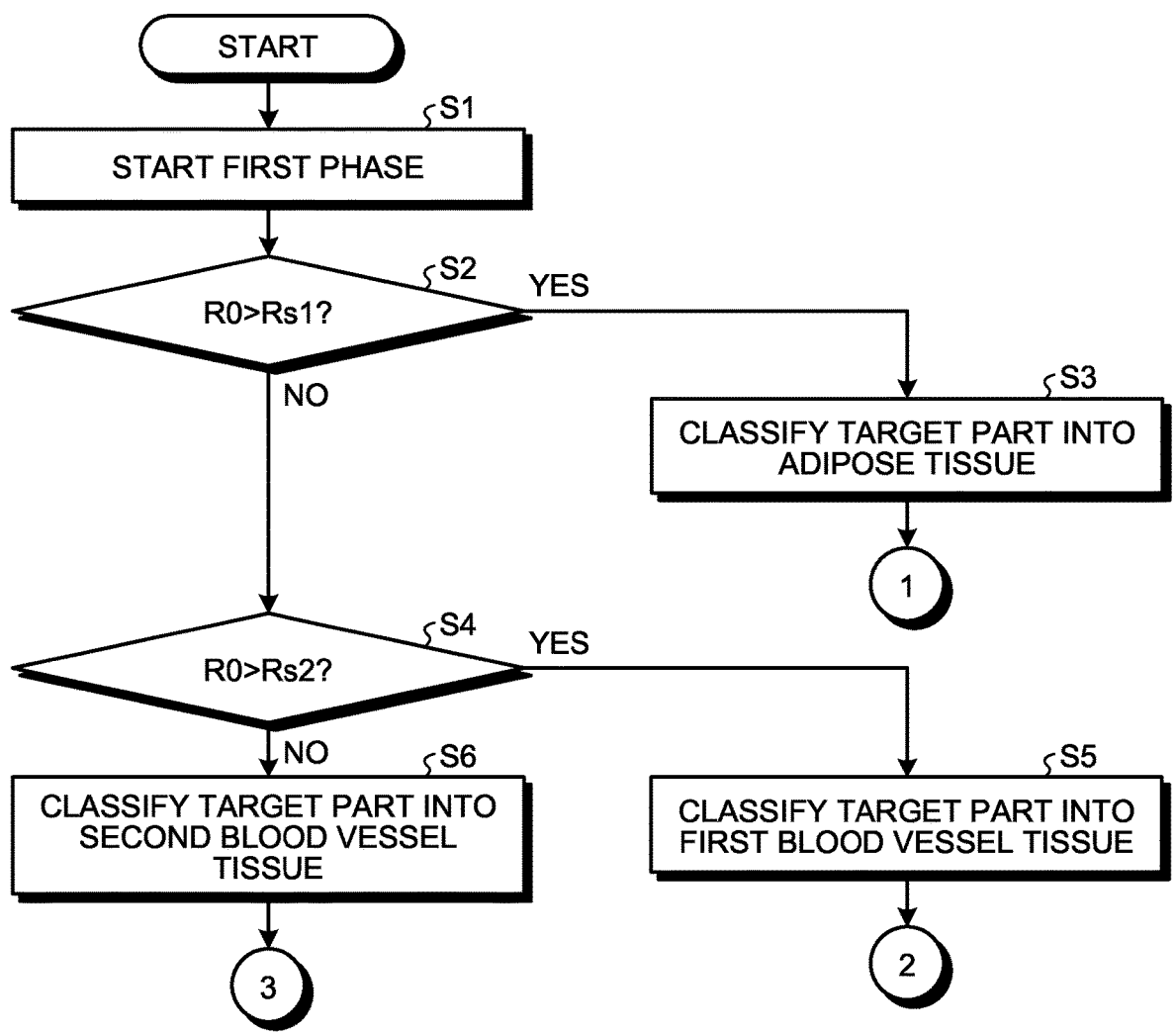
FIG. 4 is a flowchart illustrating a control method executed by a processor.

FIG. 3 is a block diagram illustrating a configuration of the control device 3.

The control device 3 integrally controls the operation of the treatment instrument 2 via the electric cable C. As illustrated in FIG. 3, the control device 3 includes a radio frequency energy output unit 31, a sensor 32, a notification unit 33, a processor 34, and a memory 35.

The radio frequency energy output unit 31 corresponds to a drive source. The radio frequency energy output unit 31 supplies radio frequency power to the first and second electrodes 12 and 15 via the pair of radio frequency lead wires C1 and C1' under the control of the processor 34. As a result, a radio frequency current flows through the target part gripped between the first and second electrodes 12 and 15. In other words, radio frequency energy is applied to the target part gripped between the first and second electrodes 12 and 15.

The sensor 32 detects a voltage value and a current value supplied from the radio frequency energy output unit 31 to the first and second electrodes 12 and 15. Then, the sensor 32 outputs a signal according to the detected voltage value and current value to the processor 34.

The notification unit 33 makes notification of predetermined information under the control of the processor 34. Examples of the notification unit 33 include a light emitting diode (LED) that makes notification of predetermined information by lighting, blinking, or a color at the time of lighting, a display device that displays predetermined information, a speaker that outputs predetermined information by voice, and the like.

The processor 34 is, for example, a central processing unit (CPU), a field-programmable gate array (FPGA), or the like, and controls the entire operation of the treatment system 1 according to a program stored in the memory 35. Note that detailed functions of the processor 34 will be described in "Control method executed by processor" described later.

The memory 35 stores a program executed by the processor 34, information necessary for process of the processor 34, and the like.

In addition, the control device 3 may include an ultrasonic energy output unit (not illustrated). In a case where the first gripping member 8 is a vibration transmission member, power is supplied to the ultrasound transducer via an ultrasound lead wire (not illustrated) under the control of the processor 34. As a result, the ultrasound transducer generates ultrasound vibration, and the ultrasound vibration is applied to the target part by the vibration transmission member.

Control Method Executed by Processor

Next, a control method executed by the processor 34 will be described.

FIGS. 4 to 7 are flowcharts illustrating a control method executed by the processor 34.

The operator holds the treatment instrument 2 by hand and inserts the distal end (the grip portion 7 and part of the shaft 6) of the treatment instrument 2 into the abdominal cavity after passing through the abdominal wall using, for example, a trocar or the like. Then, the operator grips the target part with the grip portion 7 by operating the operation knob 51. In addition, the operator performs a treatment start operation with the switch 521. Accordingly, the processor 34 executes the following control method.

First, the processor 34 starts a first phase (step S1).

The first phase is a phase in which an impedance value of a target part is detected while constant power is supplied to the first and second electrodes 12 and 15, and the target part is classified (identified) into any one of a plurality of tissue types based on the impedance value.

Specifically, the processor 34 executes the following processing in the first phase.

The processor 34 supplies constant power to the first and second electrodes 12 and 15 for a constant time (for example, 100 [msec]) by controlling the operation of the radio frequency energy output unit 31. The constant power is power with such an extent to which the target part is not thermally denatured (for example, 5 [W]). In addition, the constant time corresponds to a first time period. While the constant power is supplied, the processor 34 calculates the impedance value of the target part based on the voltage value and the current value detected by the sensor 32. Then, the processor 34 sequentially stores the calculated impedance value of the target part in the memory 35. In addition, the processor 34 calculates an initial impedance value R0 by averaging the plurality of impedance values sequentially stored in the memory 35 during the last period (for example, 20 [msec]) in the first time period. The initial impedance value R0 corresponds to a first parameter.

Figure 8:
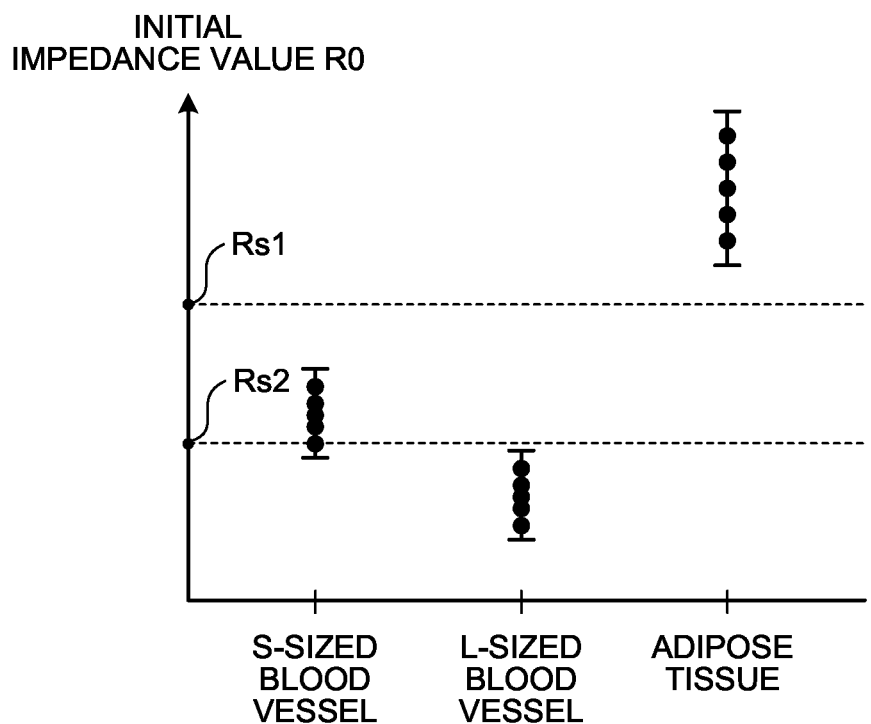
FIG. 8 is a diagram illustrating distributions of initial impedance values in an S-sized blood vessel, an L-sized blood vessel, and an adipose tissue.

FIG. 8 is a diagram illustrating the distribution of the initial impedance values R0 in each of the S-sized blood vessel, the L-sized blood vessel, and the adipose tissue.

Here, the initial impedance values R0 of the S-sized blood vessel having a small size (corresponding to a first blood vessel tissue that is a first sized blood vessel tissue) and the L-sized blood vessel having a large size (corresponding to a second blood vessel tissue that is a second sized blood vessel tissue) among the blood vessel tissues, and the adipose tissue have a tendency illustrated in FIG. 8.

Then, the processor 34 compares the initial impedance value R0 with a determination threshold value Rs1 (FIG. 8), and determines whether a relationship of R0>Rs1 is satisfied (step S2). Here, the determination threshold value Rs1 corresponds to a first impedance value, and is, for example, about 300 [Ω].

When determining that the relationship of R0>Rs1 is satisfied (step S2: Yes), the processor 34 classifies the target part into the adipose tissue (corresponding to the tissue type) (step S3).

On the other hand, when determining that the relationship of R0>Rs1 is not satisfied (step S2: No), the processor 34 compares the initial impedance value R0 with a determination threshold value Rs2 (FIG. 8), and determines whether the relationship of R0>Rs2 is satisfied (step S4). Here, the determination threshold value Rs2 is, for example, about 100 [Ω].

When determining that the relationship of R0>Rs2 is satisfied (step S4: Yes), the processor 34 classifies the target part into the first blood vessel tissue (corresponding to the tissue type) (step S5).

Even when the relationship of Rs1≥R0>Rs2 is satisfied, the target part is not necessarily the S-sized blood vessel, and may be the adipose tissue. That is, the target part cannot be appropriately classified into the S-sized blood vessel (first blood vessel tissue) simply by the initial impedance value R0.

On the other hand, when determining that the relationship of R0>Rs2 is not satisfied (step S4: No), the processor 34 classifies the target part into the second blood vessel tissue (corresponding to the tissue type) (step S6).

Even if the relationship of Rs2≥R0 is satisfied, the target part may not be necessarily the L-sized blood vessel, but may be a living tissue (hereinafter, it is described as a tissue in solution) around which a conductive solution such as blood or physiological saline is present. That is, the target part cannot be appropriately classified into the L-sized blood vessel (second blood vessel tissue) simply by the initial impedance value R0.

Hereinafter, the process after the target part is classified into the adipose tissue in the first phase (step S3), the process after the target part is classified into the first blood vessel tissue in the first phase (step S5), and the process after the target part is classified into the second blood vessel tissue in the first phase (step S6) will be sequentially described.

Process After Classification of Target Part into Adipose Tissue in First Phase

Figure 5:
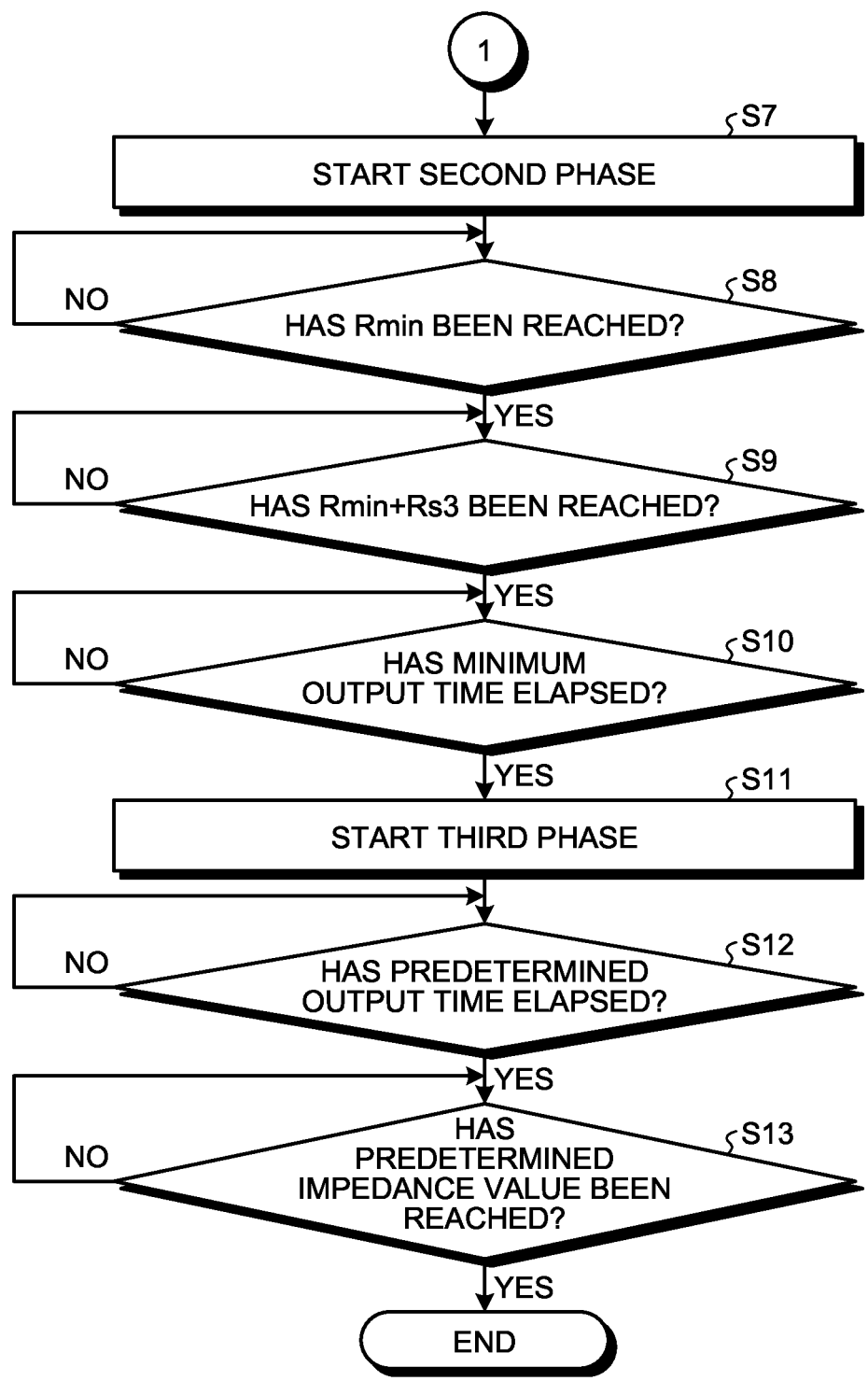
FIG. 5 is a flowchart illustrating a control method executed by a processor.

First, the process after the target part is classified into the adipose tissue (step S3) in the first phase will be described with reference to FIG. 5.

After step S3, the processor 34 ends the first phase and starts a second phase (step S7).

The second phase is a phase of uniformly heating the target part by increasing the output voltage supplied to the first and second electrodes 12 and 15 at a specific increase rate.

Meanwhile, when the output voltage supplied to the first and second electrodes 12 and 15 is rapidly increased in the second phase, the temperature of the target part is rapidly increased. That is, the target part cannot be uniformly heated. Then, the temperature unevenness is generated in the target part, and the sealing performance of the target part is deteriorated. Therefore, in the present embodiment, the processor 34 sets the increase rate to a value according to the tissue type classified in the first phase. More specifically, the processor 34 sets the increase rate to a value proportional to V(Z)/R0. Here, V(Z) is a value (for example, adipose tissue: 75, first and second blood vessel tissues: 60) according to the tissue type classified in the first phase. When compared based on the tissue type classified in the first phase, the increase rate is larger in the adipose tissue than in the first and second blood vessel tissues.

Specifically, the processor 34 executes the following processing in the second phase.

By controlling the operation of the radio frequency energy output unit 31, the processor 34 increases the output voltage supplied to the first and second electrodes 12 and 15 from the output voltage (peak value) at the end of the first phase at an increase rate according to the adipose tissue classified in the first phase. While increasing the output voltage, the processor 34 calculates the impedance value of the target part based on the voltage value and the current value detected by the sensor 32. Then, the processor 34 sequentially stores the calculated impedance value of the target part in the memory 35.

Figure 9:
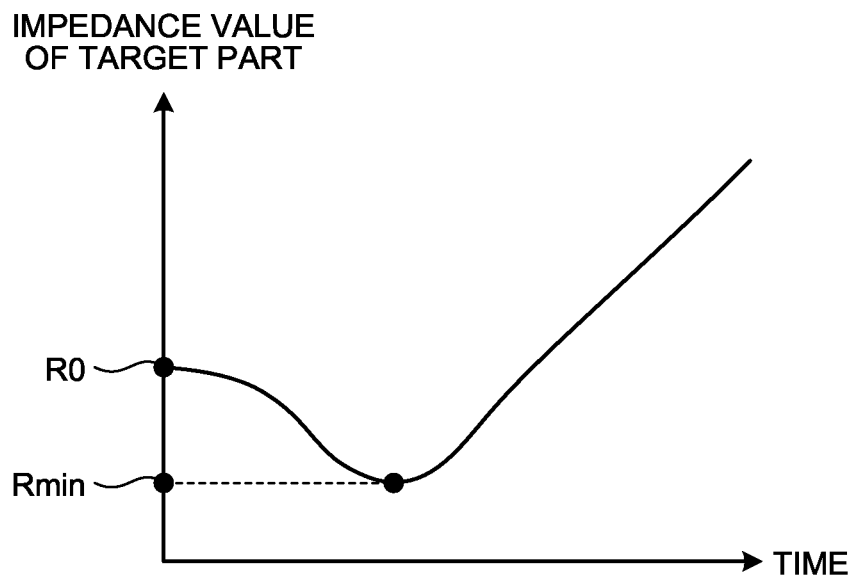
FIG. 9 is a diagram illustrating behavior of an impedance value of a target part.

FIG. 9 is a diagram illustrating the behavior of the impedance value of the target part.

When the second phase is started, the target part is heated by radio frequency energy being applied. Then, as illustrated in FIG. 9, the impedance value of the target part decreases, and takes the minimum value Rmin when the water of the target part reaches the boiling state. Further, when the heating of the target part is further continued, the water of the target part evaporates and the impedance value of the target part turns to increase.

Then, the processor 34 refers to the impedance value of the target part stored in the memory 35, and constantly monitors whether the impedance value of the target part has reached the minimum value Rmin (step S8).

When the impedance value of the target part reaches the minimum value Rmin (step S8: Yes), the processor 34 constantly monitors whether the impedance value of the target part reaches an impedance value (Rmin+Rs3) obtained by adding a specific impedance value Rs3 (for example, about 20 [Ω]) to the minimum value Rmin (step S9). When the impedance value of the target part reaches the impedance value (Rmin+Rs3), it means that the heating state has shifted to the dry state.

When the impedance value of the target part reaches the impedance value (Rmin+Rs3) (step S9: Yes), the processor 34 constantly monitors whether the elapsed time from the start of the second phase (step S7) has passed the minimum output time (for example, 1000 [msec]) according to the adipose tissue classified in the first phase (step S10).

When the elapsed time has passed the minimum output time (step S10: Yes), the processor 34 ends the second phase and starts a third phase (step S11).

The third phase is a phase in which the target part is dried to the deep portion by making the output voltage supplied to the first and second electrodes 12 and 15 constant at a specific output voltage.

Specifically, the processor 34 executes the following processing in the third phase.

The processor 34 controls the operation of the radio frequency energy output unit 31 to make the output voltage supplied to the first and second electrodes 12 and 15 constant at an output voltage (for example, 75 [V]) according to the adipose tissue classified in the first phase. While the constant output voltage is supplied to the first and second electrodes 12 and 15, the processor 34 calculates an impedance value of the target part based on the voltage value and the current value detected by the sensor 32.

Then, the processor 34 constantly monitors whether the elapsed time from the start of the third phase (step S11) has passed a predetermined output time (step S12).

When the elapsed time has passed the predetermined output time (step S12: Yes), the processor 34 constantly monitors whether the impedance value of the target part has reached a predetermined impedance value (step S13).

When the impedance value of the target part reaches the predetermined impedance value (step S13: Yes), the processor 34 ends this control flow.

Figure 10:
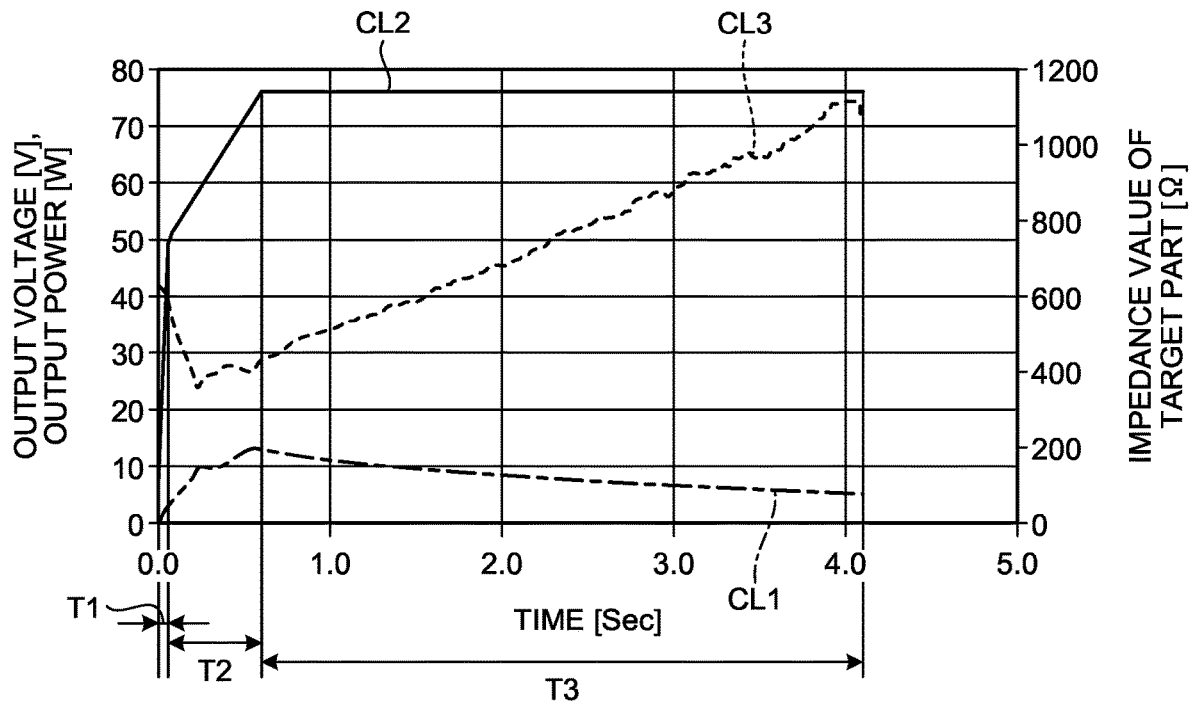
FIG. 10 is a diagram illustrating an example of behavior of output power, output voltage, and an impedance value of a target part during execution of a control method.

FIG. 10 is a diagram illustrating an example of behavior of the output power, the output voltage, and the impedance value of the target part when the control method is executed. FIG. 10 corresponds to a case where steps S1 to S3 and S7 to S13 are executed (a case where the target part is classified into the adipose tissue in the first phase). In FIG. 10, the output power is indicated by a curve CL1, the output voltage is indicated by a curve CL2, and the impedance value of the target part is indicated by a curve CL3.

As illustrated in FIG. 10, in a case where the target part is classified into the adipose tissue in the first phase (first time period T1), in the second phase (second time period T2), the output voltage supplied to the first and second electrodes 12 and 15 is increased from the output voltage (peak value) at the end of the first phase at an increase rate according to the adipose tissue. Thereafter, in the third phase (third time period T3), constant voltage control is performed with an output voltage (for example, 75 [V]) according to the adipose tissue. As a result, the target part (adipose tissue) is sealed.

Process After Classification into First Blood Vessel Tissue in First Phase

Figure 6:
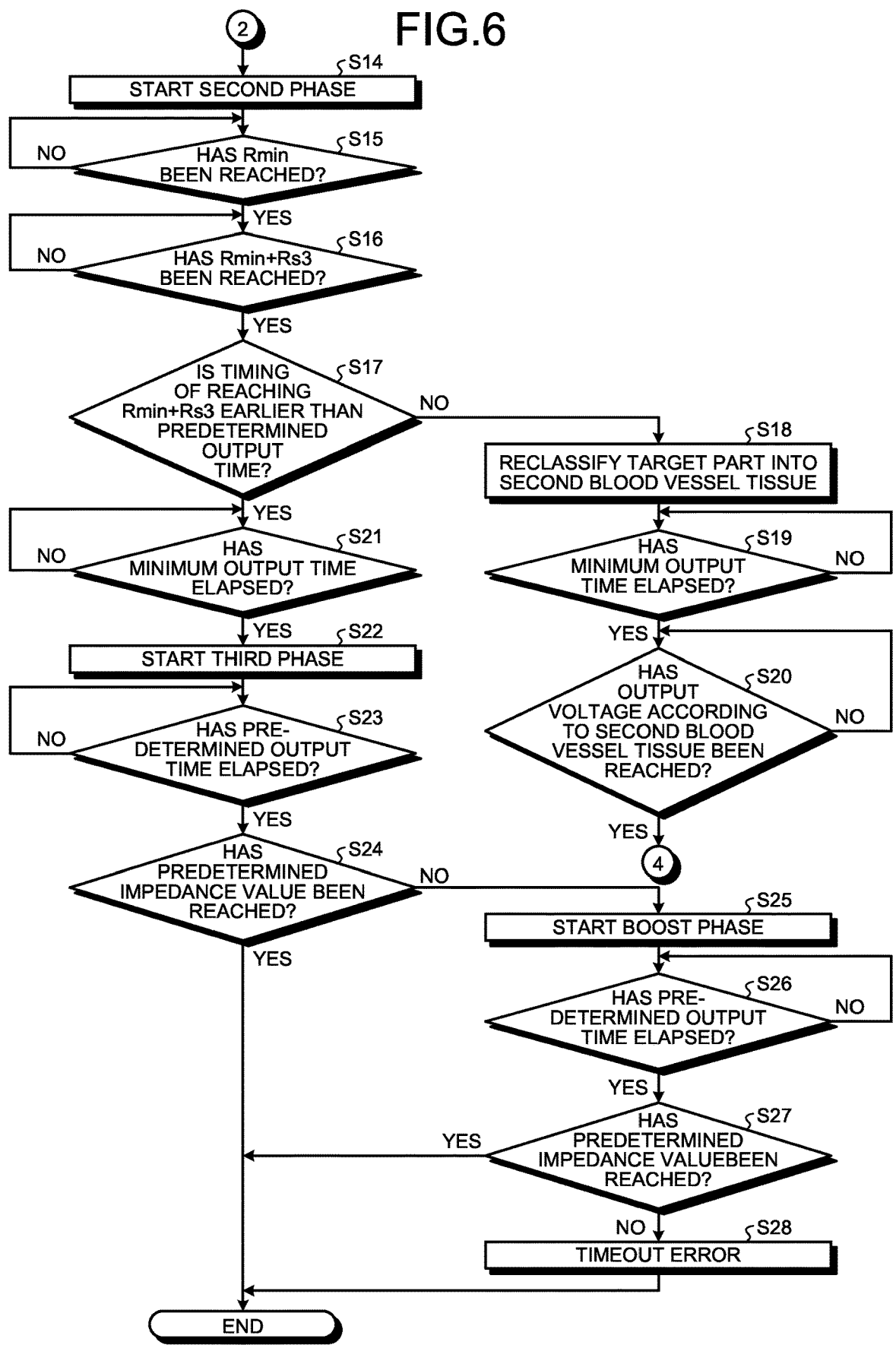
FIG. 6 is a flowchart illustrating a control method executed by a processor.

Next, the process after the target part is classified into the first blood vessel tissue (step S5) in the first phase will be described with reference to FIG. 6.

After step S5, the processor 34 ends the first phase and starts the second phase as in step S7 (step S14).

When the target part is classified into the first blood vessel tissue in the first phase, the processor 34 increases, in the second phase, the output voltage supplied to the first and second electrodes 12 and 15 from the output voltage lower than the peak value of the output voltage in the first phase at an increase rate according to the first blood vessel tissue classified in the first phase. As described above, the increase rate is set to a value (for example, V(Z)=60) proportional to V(Z)/R0. That is, since the increase rate is proportional to the reciprocal of the initial impedance value R0, the larger the initial impedance value R0 is, the gentler the inclination of the increase in the output voltage is. Therefore, in a case where it is assumed that the target part has a small size sensitive to a temperature rise (in a case where the target part is classified into the first blood vessel tissue), the increase rate is set to be smaller than that in a case where the target part is assumed to have a large size (in a case where the target part is classified into the second blood vessel tissue).

Then, similarly to steps S8 and S9, the processor 34 monitors whether the impedance value of the target part has reached the minimum value Rmin and whether the impedance value of the target part has reached the impedance value (Rmin+Rs3) (steps S15 and S16).

In the first phase, the target part is classified into the first blood vessel tissue or the second blood vessel tissue according to the initial impedance value R0 in steps S4 to S6. However, as illustrated in FIG. 8, since there is an overlap in the distribution of the initial impedance values R0 between the S-sized blood vessel (first blood vessel tissue) and the L-sized blood vessel (second blood vessel tissue), the target part cannot be accurately classified into the first blood vessel tissue or the second blood vessel tissue at the initial impedance value R0.

Here, it has been experimentally found that the target part can be accurately classified into the first blood vessel tissue or the second blood vessel tissue by using the elapsed time from the start of the second phase (step S14) until the impedance value of the target part reaches the impedance value (Rmin+Rs3). Therefore, the processor 34 executes step S17 described below.

When the impedance value of the target part reaches the impedance value (Rmin+Rs3) (step S16: Yes), the processor 34 determines whether the elapsed time from the start of the second phase (step S14) until the impedance value of the target part reaches the impedance value (Rmin+Rs3) is shorter than the predetermined output time (step S17). The predetermined output time is set to a time (for example, 800 [msec]) shorter than the minimum output time (for example, 1000 [msec]) according to the second blood vessel tissue classified in the first phase used in step S32 and longer than the minimum output time (for example, 600 [msec]) according to the first blood vessel tissue classified in the first phase used in step S21.

When determining that the elapsed time is not shorter than the predetermined output time (step S17: No), the processor 34 classified the target part into the first blood vessel tissue in the first phase, but reclassifies the target part into the second blood vessel tissue (step S18). That is, the impedance value (Rmin+Rs3) corresponds to a predetermined impedance value. The elapsed time from the start of the second phase until the impedance value of the target part reaches the impedance value (Rmin+Rs3) corresponds to a parameter detected in the second time period.

After step S18, the processor 34 constantly monitors whether the elapsed time from the start of the second phase (step S14) has passed the minimum output time (for example, 1000 [msec]) according to the second blood vessel tissue reclassified in step S18 (step S19).

After step S19, the processor 34 constantly monitors whether the output voltage supplied to the first and second electrodes 12 and 15 reaches the output voltage (for example, 50 [V]) according to the second blood vessel tissue used in the third phase in step S33 (step S20).

When determining that the output voltage has reached the output voltage according to the second blood vessel tissue (step S20: Yes), the processor 34 advances the process to step S33.

When determining that the elapsed time is shorter than the predetermined output time (step S17: Yes), the processor 34 determines that the classification into the first blood vessel tissue in the first phase is appropriate. Then, the processor 34 constantly monitors whether the elapsed time from the start of the second phase (step S14) has passed the minimum output time (for example, 600 [msec]) according to the first blood vessel tissue (step S21).

When the elapsed time has passed the minimum output time (step S21: Yes), the processor 34 ends the second phase and starts the third phase as in step S11 (step S22).

When the target part is classified into the first blood vessel tissue in the first phase, the processor 34 makes, in the third phase, the output voltage supplied to the first and second electrodes 12 and 15 constant at the output voltage (for example, 35 [V]) according to the first blood vessel tissue.

Then, the processor 34 constantly monitors whether the elapsed time from the start of the third phase (step S22) has passed a predetermined output time (step S23).

As described above, the target part cannot be accurately classified into the S-sized blood vessel (first blood vessel tissue) or the adipose tissue by the initial impedance value R0.

Here, it has been experimentally found that the target part can be accurately classified into the S-sized blood vessel (first blood vessel tissue) or the adipose tissue by using the impedance value (corresponding to the second parameter (parameter detected in the third time period)) of the target part after the predetermined output time elapses (step S23: Yes) from the start of the third phase (step S22). Therefore, the processor 34 executes step S24 described below.

When the elapsed time has passed the predetermined output time (step S23: Yes), the processor 34 determines whether the impedance value of the target part has reached a predetermined impedance value (step S24).

When determining that the impedance value of the target part has reached the predetermined impedance value (step S24: Yes), the processor 34 classifies the target part into the S-sized blood vessel (first blood vessel tissue), and ends this control flow.

Figure 11:
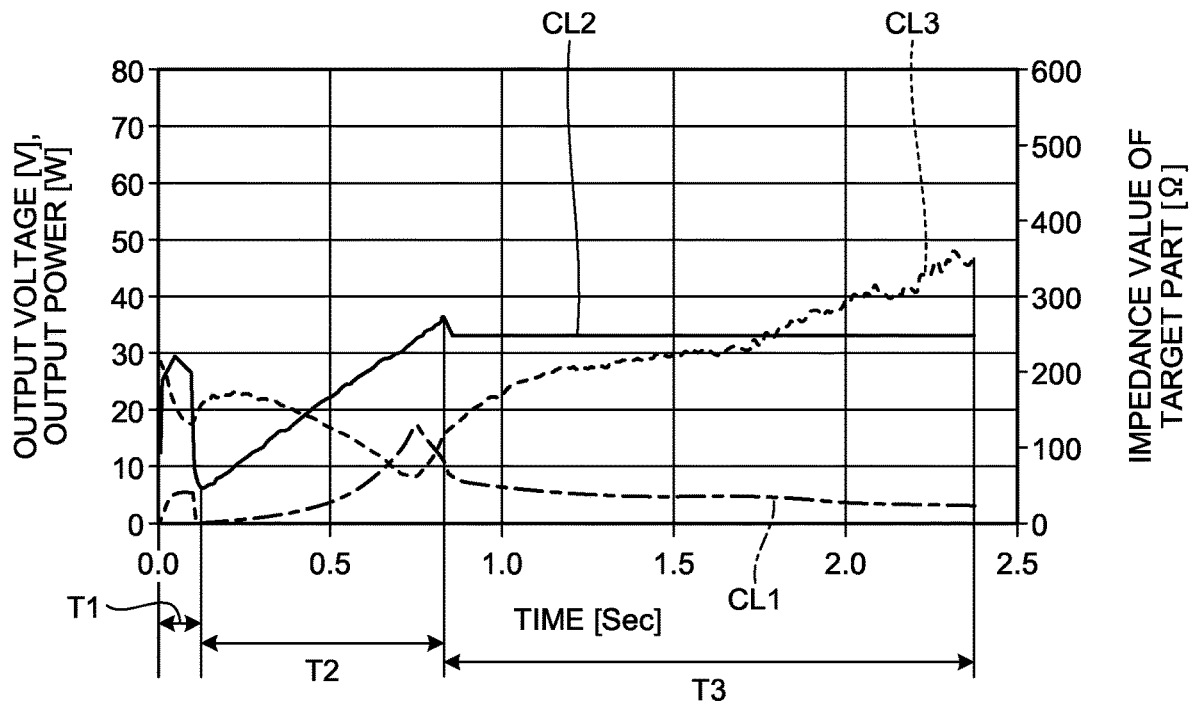
FIG. 11 is a diagram illustrating an example of behavior of output power, output voltage, and an impedance value of a target part during execution of a control method.

FIG. 11 is a diagram illustrating an example of behavior of the output power, the output voltage, and the impedance value of the target part when the control method is executed. Note that FIG. 11 corresponds to a case where steps S1, S2, S4, S5, S14 to S17, and S21 to S24 are executed (when the target part is classified into the first blood vessel tissue in the first phase to when the classification into the first blood vessel tissue in the first phase is determined to be appropriate in the second phase to when the target part is classified into the first blood vessel tissue in the third phase). In FIG. 11, the output power is indicated by the curve CL1, the output voltage is indicated by the curve CL2, and the impedance value of the target part is indicated by the curve CL3.

As illustrated in FIG. 11, when the target part is classified into the first blood vessel tissue in the first phase (first time period T1), in the second phase (second time period T2), the output voltage supplied to the first and second electrodes 12 and 15 is increased from the output voltage lower than the peak value of the output voltage in the first phase at an increase rate according to the first blood vessel tissue. When it is determined that the classification into the first blood vessel tissue in the first phase (first time period T1) is appropriate (second phase (second time period T2)), constant voltage control is performed with an output voltage (for example, 35 [V]) according to the first blood vessel tissue in the third phase (third time period T3). Then, when the predetermined impedance value is reached, it is finally determined that the target part is the first blood vessel tissue, and the constant voltage control is terminated. As a result, the target part (S-sized blood vessel) is sealed.

On the other hand, when determining that the impedance value of the target part has not reached the predetermined impedance value (step S24: No), the processor 34 classifies the target part into the adipose tissue (corresponding to the tissue type). Then, the processor 34 ends the third phase and starts the boost phase (step S25).

The boost phase is a phase in which the application of the radio frequency energy is continued as the target part is not the S-sized blood vessel (first blood vessel tissue) but the adipose tissue.

Specifically, the processor 34 executes the following processing in the boost phase.

By controlling the operation of the radio frequency energy output unit 31, the processor 34 increases the output voltage supplied to the first and second electrodes 12 and 15 from the output voltage at the end of the third phase at the same increase rate as the increase rate used in the second phase (step S14) until the supplied output voltage reaches the output voltage (for example, 75 [V]) according to the adipose tissue used in step S11. Then, when the output voltage supplied to the first and second electrodes 12 and 15 reaches the output voltage (for example, 75 [V]) according to the adipose tissue, the processor 34 makes the supplied output voltage constant at the output voltage according to the adipose tissue. During the above processes, the processor 34 calculates the impedance value of the target part based on the voltage value and the current value detected by the sensor 32.

Then, the processor 34 constantly monitors whether the elapsed time from the start of the boost phase (step S25) has passed a predetermined output time (step S26).

When the elapsed time has passed the predetermined output time (step S26: Yes), the processor 34 determines whether the impedance value of the target part has reached a predetermined impedance value (step S27).

When determining that the impedance value of the target part has reached the predetermined impedance value (step S27: Yes), the processor 34 ends this control flow.

Figure 12:
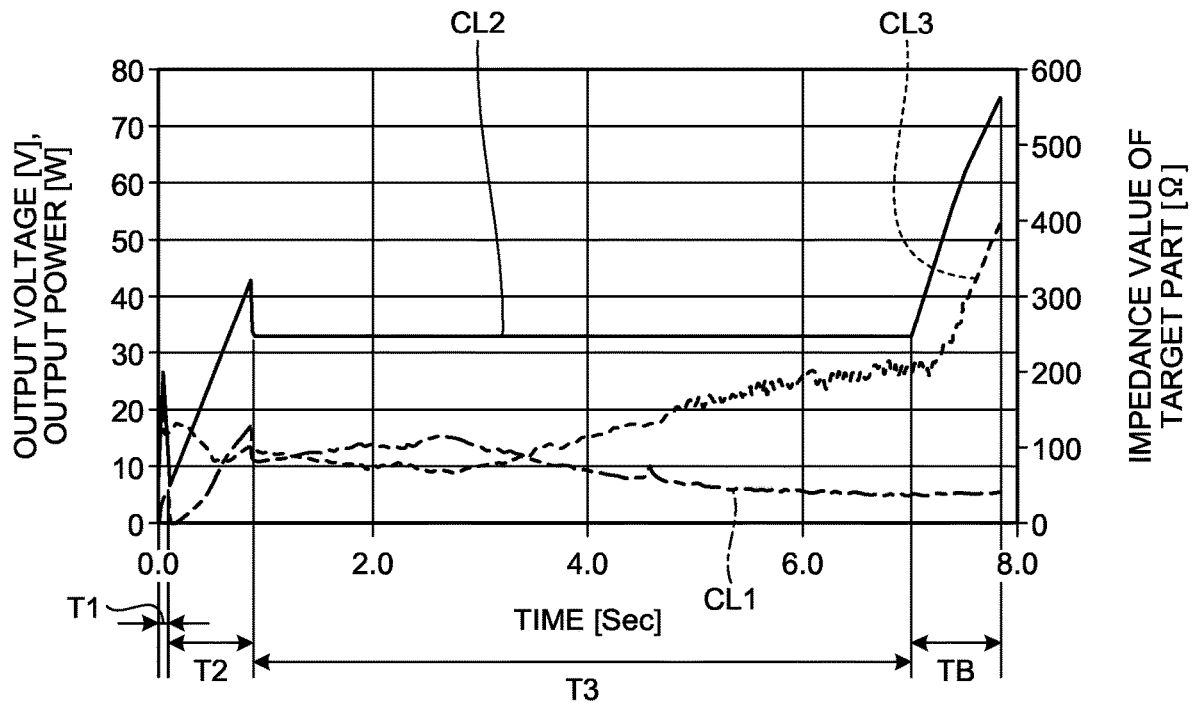
FIG. 12 is a diagram illustrating an example of behavior of output power, output voltage, and an impedance value of a target part during execution of a control method.

FIG. 12 is a diagram illustrating an example of behavior of the output power, the output voltage, and the impedance value of the target part when the control method is executed. Note that FIG. 12 corresponds to a case where steps S1, S2, S4, S5, S14 to 517, and S21 to S27 are executed (when the target part is classified into the first blood vessel tissue in the first phase to when the classification into the first blood vessel tissue in the first phase is determined to be appropriate in the second phase to when the target part is classified into the adipose tissue in the third phase). In FIG. 12, the output power is indicated by the curve CL1, the output voltage is indicated by the curve CL2, and the impedance value of the target part is indicated by the curve CL3.

As illustrated in FIG. 12, when the target part is classified into the first blood vessel tissue in the first phase (first time period T1), in the second phase (second time period T2), the output voltage supplied to the first and second electrodes 12 and 15 is increased from the output voltage lower than the peak value of the output voltage in the first phase at an increase rate according to the first blood vessel tissue. When it is determined that the classification into the first blood vessel tissue in the first phase (first time period T1) is appropriate (second phase (second time period T2)), constant voltage control is performed with an output voltage (for example, 35 [V]) according to the first blood vessel tissue in the third phase (third time period T3). Furthermore, in a case where the target part is classified into the adipose tissue in the third phase (third time period T3), in the boost phase (boost time period TB), the output voltage supplied to the first and second electrodes 12 and 15 is increased from the output voltage at the end of the third phase at the increase rate used in the second phase. Then, when the predetermined impedance value is reached, the boost phase (boost time period TB) is ended. As a result, the target part (adipose tissue) is sealed.

On the other hand, when determining that the impedance value of the target part has not reached the predetermined impedance value (step S27: No), the processor 34 causes the notification unit 33 to make notification of information indicating a warning (timeout error) (step S28). Thereafter, the processor 34 ends this control flow.

Process After Classification into Second Blood Vessel Tissue in First Phase

Figure 7:
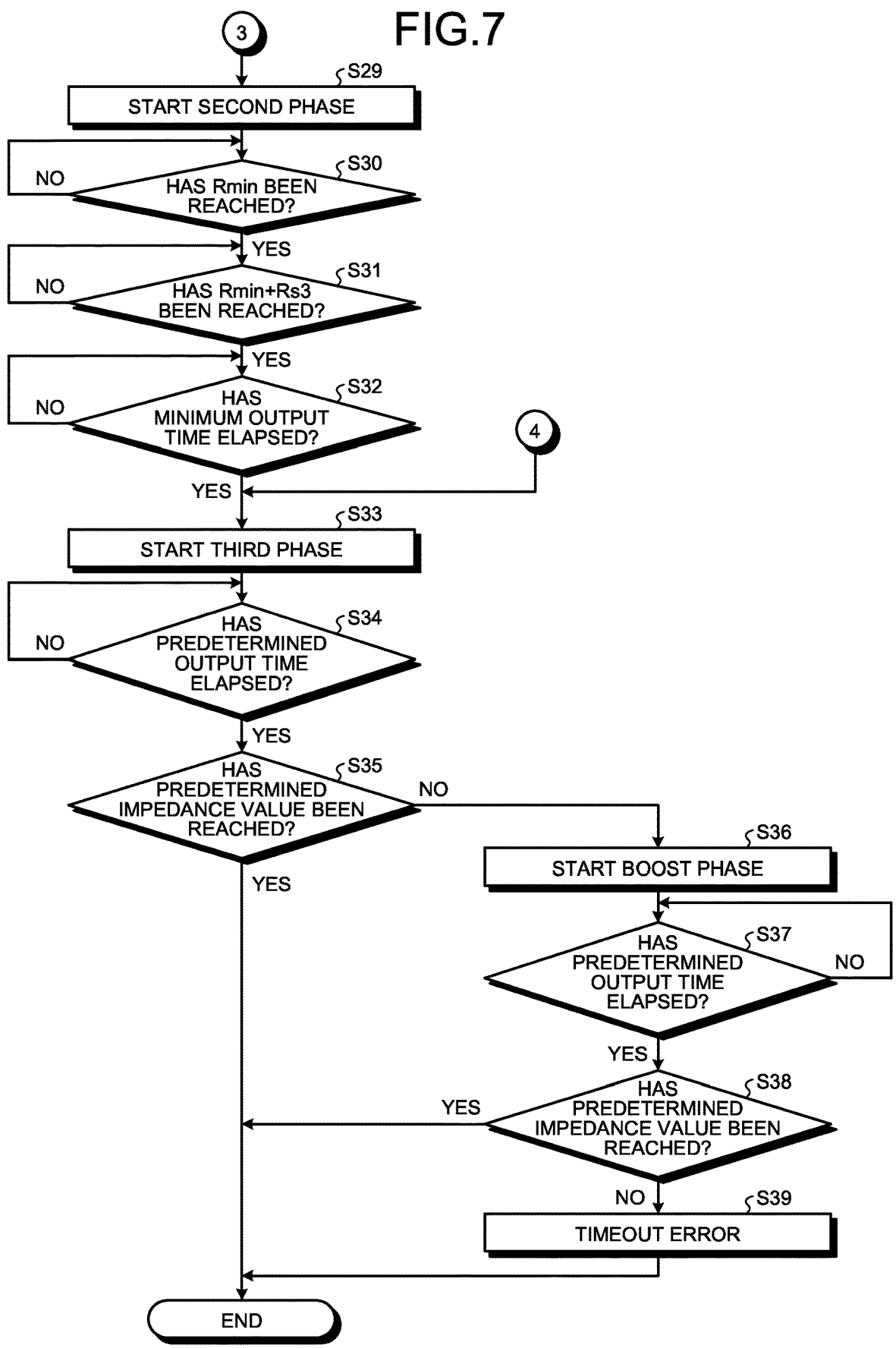
FIG. 7 is a flowchart illustrating a control method executed by a processor.

Next, the process after the target part is classified into the second blood vessel tissue (step S6) in the first phase will be described with reference to FIG. 7.

After step S6, the processor 34 ends the first phase and starts the second phase as in steps S7 and S14 (step S29).

When the target part is classified into the second blood vessel tissue in the first phase, the processor 34 increases, in the second phase, the output voltage supplied to the first and second electrodes 12 and 15 from the output voltage lower than the peak value of the output voltage in the first phase at an increase rate according to the second blood vessel tissue classified in the first phase, as in a case where the target part is classified into the first blood vessel tissue in the first phase. As described above, the increase rate is set to a value (for example, V(Z)=60) proportional to V(Z)/R0.

Then, similarly to steps S8 and S9, the processor 34 monitors whether the impedance value of the target part has reached the minimum value Rmin and whether the impedance value of the target part has reached the impedance value (Rmin+Rs3) (steps S30 and S31).

After step S31, the processor 34 constantly monitors whether the elapsed time from the start of the second phase (step S29) has passed the minimum output time (for example, 1000 [msec]) according to the second blood vessel tissue classified in the first phase (step S32).

When the elapsed time has passed the minimum output time (step S32: Yes) or when it is determined that the output voltage has reached the output voltage according to the second blood vessel tissue (step S20: Yes), the processor 34 ends the second phase and starts the third phase as in steps S11 and S22 (step S33).

When the target part is classified into the second blood vessel tissue in the first phase, the processor 34 makes, in the third phase, the output voltage supplied to the first and second electrodes 12 and 15 constant at the output voltage (for example, 50 [V]) according to the second blood vessel tissue.

Then, the processor 34 constantly monitors whether the elapsed time from the start of the third phase (step S33) has passed a predetermined output time (step S34).

As described above, the target part cannot be accurately classified into the L-sized blood vessel (second blood vessel tissue) or the tissue in solution by the initial impedance value R0.

Here, it has been experimentally found that the target part can be accurately classified into the L-sized blood vessel (second blood vessel tissue) or the tissue in solution by using the impedance value (corresponding to the second parameter (parameter detected in the third time period)) of the target part after the predetermined output time elapses (step S34: Yes) from the start of the third phase (step S33). Therefore, the processor 34 executes step S35 described below.

When the elapsed time has passed the predetermined output time (step S34: Yes), the processor 34 determines whether the impedance value of the target part has reached a predetermined impedance value (step S35).

When determining that the impedance value of the target part has reached the predetermined impedance value (step S35: Yes), the processor 34 classifies the target part into the L-sized blood vessel (second blood vessel tissue), and ends this control flow.

Figure 13:
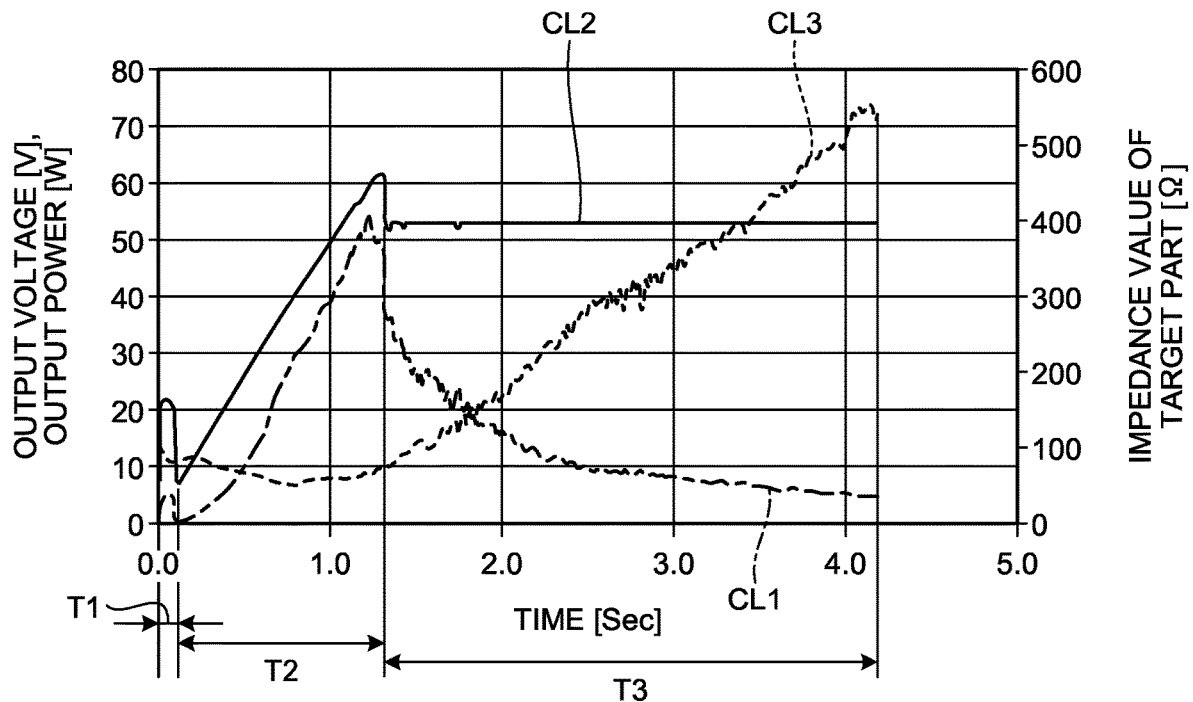
FIG. 13 is a diagram illustrating an example of behavior of output power, output voltage, and an impedance value of a target part during execution of a control method.

FIG. 13 is a diagram illustrating an example of behavior of the output power, the output voltage, and the impedance value of the target part when the control method is executed. Note that FIG. 13 corresponds to a case where steps S1, S2, S4, S6, and S29 to S35 are executed (when the target part is classified into the second blood vessel tissue in the first phase to when the target part is classified into the second blood vessel tissue in the third phase). In FIG. 13, the output power is indicated by the curve CL1, the output voltage is indicated by the curve CL2, and the impedance value of the target part is indicated by the curve CL3.

As illustrated in FIG. 13, when the target part is classified into the second blood vessel tissue in the first phase (first time period T1), in the second phase (second time period T2), the output voltage supplied to the first and second electrodes 12 and 15 is increased from the output voltage lower than the peak value of the output voltage in the first phase at an increase rate according to the second blood vessel tissue. Thereafter, in the third phase (third time period T3), constant voltage control is performed with an output voltage (for example, 50 [V]) according to the second blood vessel tissue. Then, when the predetermined impedance value is reached, it is finally determined that the target part is the second blood vessel tissue, and the constant voltage control is terminated. As a result, the target part (L-sized blood vessel) is sealed.

On the other hand, when determining that the impedance value of the target part has not reached the predetermined impedance value (step S35: No), the processor 34 classifies the target part into a tissue in solution (corresponding to the tissue type). Then, the processor 34 ends the third phase and starts the boost phase as in step S25 (step S36).

When the target part is classified into the tissue in solution in the third phase, the processor 34 sets the increase rate of the output voltage supplied to the first and second electrodes 12 and 15 to the increase rate used in the second phase (step S29) in the boost phase.

Then, the processor 34 constantly monitors whether the elapsed time from the start of the boost phase (step S36) has passed a predetermined output time (step S37).

When the elapsed time has passed the predetermined output time (step S37: Yes), the processor 34 determines whether the impedance value of the target part has reached a predetermined impedance value (step S38).

When it is determined that the impedance value of the target part has reached the predetermined impedance value (step S38: Yes), the processor 34 ends this control flow.

Figure 14:
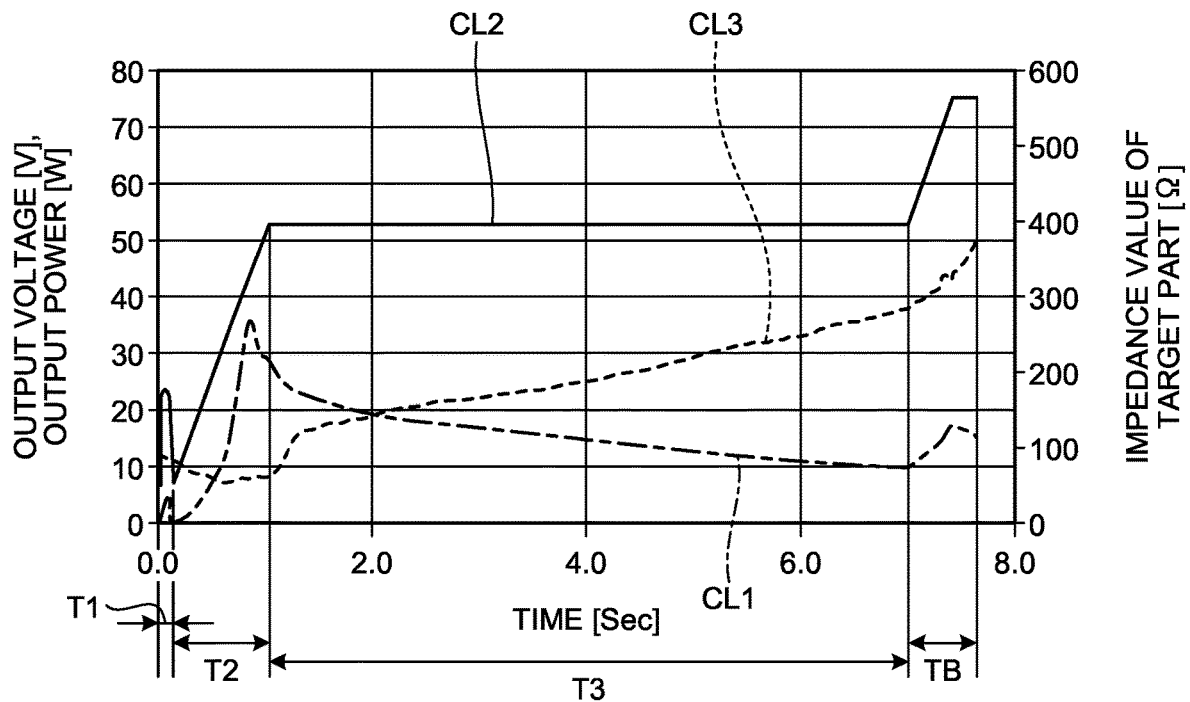
FIG. 14 is a diagram illustrating an example of behavior of output power, output voltage, and an impedance value of a target part during execution of a control method.

FIG. 14 is a diagram illustrating an example of behavior of the output power, the output voltage, and the impedance value of the target part when the control method is executed. Note that FIG. 14 corresponds to a case where steps S1, S2, S4, S6, and S29 to S38 are executed (when the target part is classified into the second blood vessel tissue in the first phase to when the target part is classified into the tissue in solution in the third phase). In FIG. 14, the output power is indicated by the curve CL1, the output voltage is indicated by the curve CL2, and the impedance value of the target part is indicated by the curve CL3.

As illustrated in FIG. 14, when the target part is classified into the second blood vessel tissue in the first phase (first time period T1), in the second phase (second time period T2), the output voltage supplied to the first and second electrodes 12 and 15 is increased from the output voltage lower than the peak value of the output voltage in the first phase at an increase rate according to the second blood vessel tissue. Thereafter, in the third phase (third time period T3), constant voltage control is performed with an output voltage (for example, 50 [V]) according to the second blood vessel tissue. Furthermore, when the target part is classified into the tissue in solution in the third phase (third time period T3), in the boost phase (boost time period TB), the output voltage supplied to the first and second electrodes 12 and 15 is increased from the output voltage at the end of the third phase at the increase rate used in the second phase. Then, when the predetermined impedance value is reached, the boost phase (boost time period TB) is ended. As a result, the target part (tissue in solution) is sealed.

On the other hand, when determining that the impedance value of the target part has not reached the predetermined impedance value (step S38: No), the processor 34 causes the notification unit 33 to make notification of information indicating a warning (timeout error) (step S39). Thereafter, the processor 34 ends this control flow.

According to the present embodiment described above, the following effects are obtained.

In the treatment system 1 according to the present embodiment, the processor 34 classifies the target part into any one of a plurality of tissue types based on the initial impedance value R0 in the first time period T1. Then, the processor 34 controls the operation of the radio frequency energy output unit 31 after the first time period T1 based on the classified tissue type. In addition, in the third time period T3, the processor 34 reclassifies the target part classified into any one of the plurality of tissue types in the first time period T1 into any one of the plurality of tissue types based on the impedance value of the target part after the lapse of the predetermined output time from the start of the third phase. Then, the processor 34 controls the operation of the radio frequency energy output unit 31 based on the tissue type into which the target part is reclassified.

Therefore, since the tissue type of the target part is appropriately classified and the operation of the radio frequency energy output unit 31 is controlled according to the classified tissue type, the target part can be appropriately treated.

In addition, in the second time period T2 (step S17), the processor 34 reclassifies the target part into any one of the plurality of tissue types based on the elapsed time from the start of the second phase until the impedance value of the target part reaches the impedance value (Rmin+Rs3).

Therefore, the target part can be classified into a more appropriate tissue type, and the target part can be more appropriately treated.

In addition, in a case where the target part is classified into the adipose tissue in the first time period T1, the processor 34 increases, in the second time period T2, the output voltage supplied to the first and second electrodes 12 and 15 from the output voltage at the end of the first time period T1 at an increase rate according to the adipose tissue.

Therefore, as compared with a configuration in which the output voltage supplied to the first and second electrodes 12 and 15 is increased from the output voltage lower than the peak value of the output voltage in the first time period T1, the target part can be treated more quickly.

In addition, in a case where the target part is classified into the adipose tissue or the tissue in solution in the third time period T3, the processor 34 continues to apply treatment energy to the target part in the boost time period TB.

Therefore, even in the target part (the adipose tissue and the tissue in solution) in which the treatment is incomplete in the first to third time periods T1 to T3, the treatment can be completed by the boost time period TB.

OTHER EMBODIMENTS

Although the embodiments for carrying out the disclosure have been described so far, the disclosure should not be limited simply by the above-described embodiments.

In the above-described embodiment, the initial impedance value R0 is adopted as the first parameter, but the disclosure is not limited thereto.

For example, in order to calculate the initial impedance value R0 of the target part based on the voltage value and the current value detected by the sensor 32 in the first phase (first time period T1), the voltage value (output voltage) and the current value (output current) detected by the sensor 32 may be set as the first parameter, and the target part may be classified into any one of a plurality of tissue types (adipose tissue, first and second blood vessel tissues, tissue in solution) based on the voltage value and the current value.

Figure 15:
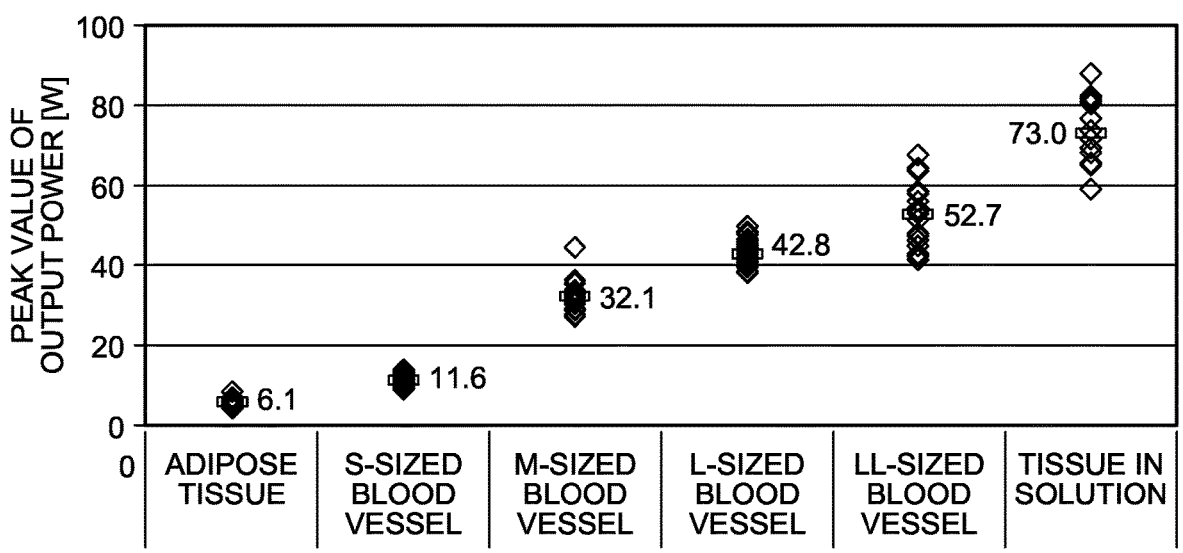
FIG. 15 is a diagram illustrating a first modification of the embodiment.

FIG. 15 is a diagram illustrating the first modification of the present embodiment. Specifically, FIG. 15 is a diagram illustrating distributions of peak values of output power in the second phase (second time period T2) in the adipose tissue, the S-sized blood vessel, the M-sized blood vessel, the L-sized blood vessel, the LL-sized blood vessel, and the tissue in solution. The M-sized blood vessel is a blood vessel tissue having a size between the size of the S-sized blood vessel and the size of the L-sized blood vessel. The LL-sized blood vessel is a blood vessel tissue larger in size than the L-sized blood vessel.

In the above-described embodiment, as the "parameter detected in the second time period", the elapsed time from the start of the second phase until the impedance value of the target part reaches the impedance value (Rmin+Rs3) is adopted, but the disclosure is not limited thereto.

Peak values of the output power in the second phase in the adipose tissue, the S-sized blood vessel, the M-sized blood vessel, the L-sized blood vessel, the LL-sized blood vessel, and the tissue in solution have a tendency illustrated in FIG. 15. Specifically, there is no overlap in the distribution of the peak values of the output power between the S-sized blood vessel and other blood vessel tissues such as the L-sized blood vessel. Therefore, the peak value of the output power calculated from the voltage value and the current value detected by the sensor 32 in the second phase is set as the "parameter detected in the second time period", and for example, the target part may be reclassified into any one of the plurality of tissue types by using the peak value instead of step S17.

Note that the peak value may be set as the second parameter, and the target part classified into any one of the plurality of tissue types may be reclassified into any one of the plurality of tissue types based on the peak value.

Figure 16:
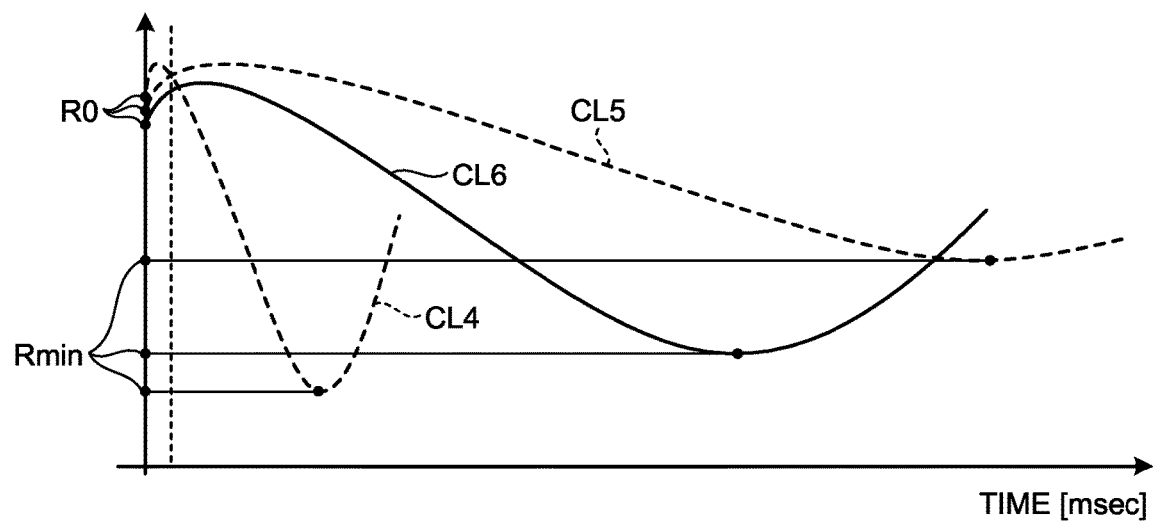
FIG. 16 is a diagram illustrating a second modification of the embodiment.

FIG. 16 is a diagram illustrating the second modification of the present embodiment. Specifically, FIG. 16 is a diagram illustrating the behavior of the impedance value of the target part.

In the above-described embodiment, as the "parameter detected in the second time period", the elapsed time from the start of the second phase until the impedance value of the target part reaches the impedance value (Rmin+Rs3) is adopted, but the disclosure is not limited thereto.

When the tissue type of the target part is different, the behavior of the impedance value is also different as illustrated in FIG. 16. In FIG. 16, the behavior of the impedance value in a case where the target part is the adipose tissue is indicated by a curve CL4, the behavior of the impedance value in a case where the target part is the tissue in solution is indicated by a curve CL5, and the behavior of the impedance value in a case where the target part is the blood vessel tissue is indicated by a curve CL6. Therefore, the variation amount (for example, R0/Rmin) of the impedance values of the target part in the second phase is set as the "parameter detected in the second time period", and for example, the target part may be reclassified into any one of the plurality of tissue types by using the variation amount instead of step S17.

Instead of R0/Rmin, the variation amount of the impedance values calculated in each of a plurality of periods until the minimum value Rmin is reached may be adopted as the "parameter detected in the second time period".

In addition, the above-described variation amount may be set as the second parameter, and the target part classified into any one of the plurality of tissue types may be reclassified into any one of the plurality of tissue types based on the variation amount.

Figure 17:
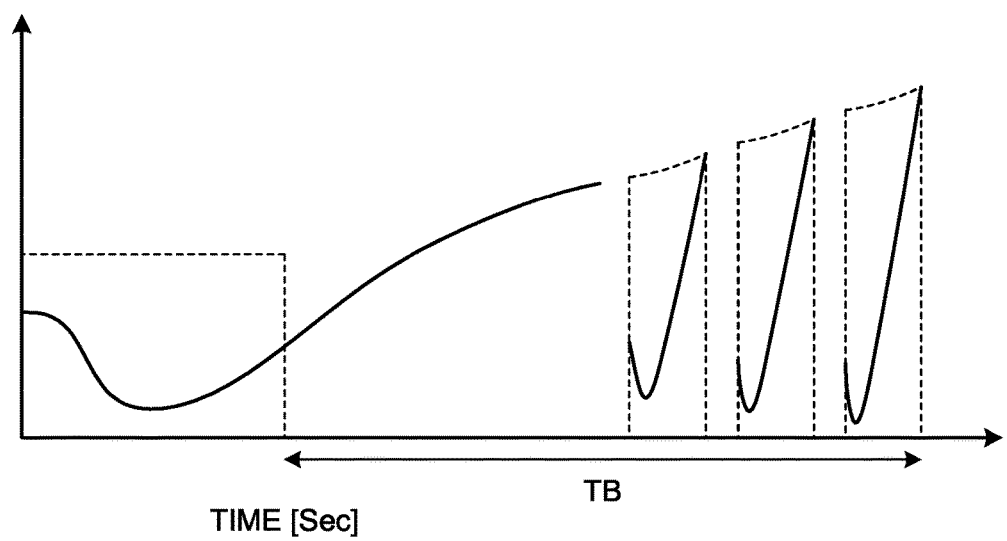
FIG. 17 is a diagram illustrating a third modification of the embodiment.

FIG. 17 is a diagram illustrating the third modification of the present embodiment. Specifically, FIG. 17 is a diagram illustrating the behavior of the impedance value of the target part.

A configuration (configuration in which radio frequency energy is intermittently applied to the target part) may be adopted in which in the boost phase (boost time period TB) according to the above-described embodiment, as illustrated in FIG. 17, the operation of the radio frequency energy output unit 31 may be stopped when the impedance value of the target part reaches a specific impedance value, and the supply of the output voltage from the radio frequency energy output unit 31 may be resumed when the impedance value of the target part sufficiently decreases. According to this configuration, since the output voltage is supplied in a state where the impedance value of the target part is low, the radio frequency current can be effectively flown to the target part, and the target part can be efficiently sealed.

In the above-described embodiment, the radio frequency energy is adopted as the treatment energy applied to the target part, but the disclosure is not limited thereto, and thermal energy or ultrasonic energy other than the radio frequency energy may be adopted. Note that "applying thermal energy to a target part" means transmitting heat of a heater or the like to the target part. In addition, "applying ultrasonic energy to a target part" means applying ultrasound vibration to the target part. A boost phase (boost time period TB) can be exemplified as the timing of applying the thermal energy or the ultrasonic energy to the target part.

According to the medical device and the control method of the disclosure, a living tissue can be appropriately treated.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical device comprising:
   an end effector configured to apply treatment energy for treating a living tissue according to supplied power;
   a drive source configured to supply the power to the end effector; and
   a processor configured to:
      classify, in a first time period after a supply of the power to the end effector is started, the living tissue into one of a plurality of tissue types based on a first parameter detected in the first time period;
      control, during a second time period after the first time period, a first operation of the drive source to increase an output voltage to be supplied to the end effector according to the classified tissue type,
      reclassify the classified living tissue into one of the plurality of tissue types based on a second parameter, the second parameter being detected in the second time period when the living tissue is classified into one of a first blood vessel tissue being a first size and second blood vessel tissue being a second size larger than the first size in the first time period, and
      control a second operation of the drive source based on the tissue type into which the classified living tissue is reclassified.

2. The medical device according to claim 1, wherein:
   the processor is configured to control, during the first time period, a third operation of the drive source to cause the drive source to supply the end effector with a constant power, and the first parameter includes an impedance value of the living tissue and an output voltage that is supplied from the drive source to the end effector.

3. The medical device according to claim 1, wherein:
   in the first time period, the living tissue is classified into one of an adipose tissue, the first blood vessel tissue, the second blood vessel tissue, and a living tissue provided in a solution that includes conductive solution.

4. The medical device according to claim 1, wherein:
   the second parameter detected in the second time period is at least one of a time until an impedance value of the living tissue reaches a predetermined impedance value, a peak value of the power supplied to the end effector, and a variation amount of impedance values of the living tissue.

5. The medical device according to claim 4, wherein:
   the living tissue is reclassified into the first blood vessel tissue when the second time period is shorter than a predetermined time and when the peak value is smaller than a predetermined peak value, and
   the living tissue is reclassified into the second blood vessel tissue when the second time period is longer than the predetermined time and when the peak value is larger than the predetermined peak value.

6. The medical device according to claim 1, wherein:
   when the living tissue is classified as an adipose tissue in the first time period, the processor is configured to increase, in the second time period, the output voltage to be supplied to the end effector at an increased rate of an output voltage according to the adipose tissue.

7. The medical device according to claim 1, wherein:
   when the living tissue is classified into the first blood vessel tissue in the first time period, the processor is configured to classify, in a third time period after the first time period, the living tissue into one of an adipose tissue and the first blood vessel tissue based on a parameter detected in the third time period, and
   when the living tissue is classified into the second blood vessel tissue in the first time period, the processor is configured to classify, in the third time period, the living tissue into one of the second blood vessel tissue and a living tissue in a solution that includes a conductive solution based on a parameter detected in the third time period.

8. The medical device according to claim 7, wherein:
   the processor is configured to control, during the third time period, a fourth operation of the drive source to cause the drive source to supply the end effector with a constant output voltage according to the classified living tissue type; and
   the parameter detected in the third time period is an impedance value of the living tissue.

9. The medical device according to claim 7, wherein
   when the living tissue is classified into the adipose tissue or the tissue in the solution in the third time period, the processor is configured to control, during a boost time period following the third time period, an operation of the drive source to continue an application of the treatment energy to the living tissue.

10. The medical device according to claim 1, further comprising a memory configured to store a plurality of impedance values of the living tissue during the first time period.

11. The medical device according to claim 10, wherein the processor is configured to calculate the first parameter by averaging the plurality of impedance values stored in the memory.

12. A control method executed by a processor of a medical device, the control method comprising:
   classifying, in a first time period after a supply of power to an end effector configured to apply treatment energy to a living tissue according to the supplied power is started, the living tissue being treated as one of a plurality of tissue types based on a first parameter detected in the first time period,
   controlling, during a second time period after the first time period, a first operation of a drive source to increase an output voltage to be supplied to the end effector according to the classified living tissue type, the drive source being configured to supply the power to the end effector;

reclassifying the classified living tissue into any one of the plurality of tissue types based on a second parameter, the second parameter being detected in the second time period when the living tissue is classified into one of a first blood vessel tissue being a first size and a second blood vessel tissue being a second size larger than the first size in the first time period; and controlling a second operation of the drive source based on the reclassified living tissue type.

13. The control method according to claim 12, wherein the second parameter is at least one of a time until an impedance value of the living tissue reaches a predetermined impedance value, a peak value of the power supplied to the end effector, and a variation amount of impedance values of the living tissue.

14. The control method according to claim 13, wherein
the living tissue is reclassified into the first blood vessel tissue when the second time period is shorter than a predetermined time and when the peak value is smaller than a predetermined peak value, and
the living tissue is reclassified into the second blood vessel tissue when the second time period is longer than the predetermined time and when the peak value is larger than the predetermined peak value.

15. The control method according to claim 12, wherein:
the processor is configured to control, during the first time period, a third operation of the drive source to cause the drive source to supply the end effector with a constant power, and the first parameter includes an impedance value of the living tissue and an output voltage that is supplied from the drive source to the end effector.

16. A control method executed by a processor configured to control a drive source configured to supply power to an end effector configured to apply treatment energy to a plurality of living tissues, the control method comprising:
controlling the drive source with first treatment energy in a first time period;
acquiring a first parameter from impedance detected from the first treatment energy;
updating a setting of second treatment energy according to the plurality of living tissues in a second time period after the first time period based on a first determination value and the first parameter;
controlling the drive source with the second treatment energy in the second time period to increase an output voltage to be supplied to the end effector according to the plurality of living tissues;
monitoring impedance detected in the second treatment energy with a second determination value, the second determination value being detected in the second time period when the living tissue is classified into one of a first blood vessel tissue being a first size and a second blood vessel tissue being a second size larger than the first size in the first time period;
updating a setting of third treatment energy according to the plurality of living tissues in a third time period after the second time period based on an elapsed time of the second time period and a monitoring result of the second determination value;
controlling the drive source with the third treatment energy in the third time period; and
controlling an operation of the drive source based on impedance detected in the third treatment energy and an elapsed time of the third time period.

17. The control method according to claim 16, wherein the second determination value is at least one of a time until an impedance value of the plurality of living tissues reaches a predetermined impedance value, a peak value of the power supplied to the end effector, and a variation amount of impedance values of the plurality of living tissues.

18. The control method according to claim 17, wherein
the plurality of living tissues are reclassified into the first blood vessel tissue when the second time period is shorter than a predetermined time and when the peak value is smaller than a predetermined peak value, and
the plurality of living tissues are reclassified into the second blood vessel tissue when the second time period is longer than the predetermined time and when the peak value is larger than the predetermined peak value.

19. The control method according to claim 16, wherein:
the processor is configured to control, during the first time period, a third operation of the drive source to cause the drive source to supply the end effector with a constant power, and the first parameter includes an impedance value of the living tissue and an output voltage that is supplied from the drive source to the end effector.

* * * * *